US012741041B2

(12) United States Patent
Geurtsen

(10) Patent No.: US 12,741,041 B2
(45) Date of Patent: Sep. 22, 2026

(54) HIGH PRESSURE-PROCESSED ARCHITECTURAL COATING COMPOSITIONS AND METHODS FOR HIGH PRESSURE-PROCESSING OF ARCHITECTURAL COATING COMPOSITIONS

(71) Applicant: Columbia Insurance Company, Omaha, NE (US)

(72) Inventor: Richard Geurtsen, Robbinsville, NJ (US)

(73) Assignee: Columbia Insurance Company, Omaha, NE (US)

( * ) Notice: Subject to any disclaimer, the term of this patent is extended or adjusted under 35 U.S.C. 154(b) by 536 days.

(21) Appl. No.: 18/269,650

(22) PCT Filed: Dec. 14, 2021

(86) PCT No.: PCT/US2021/063275

§ 371 (c)(1),
(2) Date: Jun. 26, 2023

(87) PCT Pub. No.: WO2022/146671

PCT Pub. Date: Jul. 7, 2022

(65) Prior Publication Data

US 2024/0058484 A1 Feb. 22, 2024

Related U.S. Application Data

(60) Provisional application No. 63/132,814, filed on Dec. 31, 2020.

(51) Int. Cl.
*A61L 2/04* (2006.01)
*A61L 2/081* (2026.01)
(Continued)

(52) U.S. Cl.
CPC ................ *A61L 2/04* (2013.01); *A61L 2/081* (2013.01); *A61L 2/085* (2013.01); *A61L 2/087* (2013.01);
(Continued)

(58) Field of Classification Search
CPC . A61L 2/04; A61L 2/081; A61L 2/085; A61L 2/087; A61L 2/10; A61L 2/12; A61L 2/18; A61L 2202/20; C09D 5/14
See application file for complete search history.

(56) References Cited

U.S. PATENT DOCUMENTS

2014/0010930 A1* 1/2014 Barbeau ............... A61K 8/9789 426/240
2014/0227405 A1* 8/2014 Beland ..................... A23B 2/40 426/240
(Continued)

FOREIGN PATENT DOCUMENTS

CA 198537 A 3/1920
CN 107982400 A 5/2018
(Continued)

OTHER PUBLICATIONS

European Office Action issued in connection with the corresponding European Patent Application No. 21 841 094.2 on Apr. 4, 2024.
(Continued)

*Primary Examiner* — Maris R Kessel
*Assistant Examiner* — Nebyate Seged
(74) *Attorney, Agent, or Firm* — The H.T. Than Law Group

(57) ABSTRACT

Disclosed herein are methods for pasteurizing or sterilizing architectural coating compositions using high pressure processing (HPP) with or without heat, radiation or other energy sources without additionally polymerizing the compositions, and storing same.

20 Claims, 3 Drawing Sheets

(51) Int. Cl.

| | |
|---|---|
| ***A61L 2/085*** | (2026.01) |
| ***A61L 2/087*** | (2026.01) |
| ***A61L 2/10*** | (2026.01) |
| ***A61L 2/12*** | (2006.01) |
| ***A61L 2/18*** | (2026.01) |
| ***C09D 5/14*** | (2006.01) |

(52) U.S. Cl.

CPC *A61L 2/10* (2013.01); *A61L 2/12* (2013.01); *A61L 2/18* (2013.01); *C09D 5/14* (2013.01)

(56) References Cited

U.S. PATENT DOCUMENTS

| | | | | |
|---|---|---|---|---|
| 2017/0106107 | A1* | 4/2017 | Demazeau | A61L 2/02 |
| 2017/0238580 | A1* | 8/2017 | Knight | A23L 2/02 |
| 2020/0164390 | A1* | 5/2020 | Tam | B05B 12/0024 |
| 2022/0161106 | A1 | 5/2022 | Barker et al. | |
| 2023/0322462 | A1* | 10/2023 | Chapalain | C08J 7/0423<br>220/359.3 |

FOREIGN PATENT DOCUMENTS

| | | | | |
|---|---|---|---|---|
| JP | 2022363502 A | 12/2022 | | |
| WO | WO-2016089696 A1 * | 6/2016 | | C09D 5/14 |

OTHER PUBLICATIONS

International Search Report and Written Opinion issued in connection with the corresponding International Application No. PCT/US2021/063275 on Mar. 25, 2022.

Machine translation of JP 2022363502 A to Udagawa.

“Retort Steriliser RK-3030”, Oct. 11, 2021, pp. 1-1, XP055900091, Tokyo, Japan.

Ludwig Horst et al. “Pressure inactivation of microorganisms”, High Pressure Research, vol. 12, No. 4-6. Nov. 1, 1994, pp. 193-197, XO055899818.

Butz P. et al. “Pressure inactivation of microorganisms at moderate temperature”. Physica B + C, North-Holland, Amsterdam, NL, vol. 139-140, May 1, 1986, pp. 875-877, XP024639754.

Machine translation of CN 107982400 A to Zhang.

Gonzalez et al. Effect of High-Pressure Processing on Strains of Enterobacter Sakazakii:, Journal of Food Protection, International Association for Food Protection, US, vol. 69, No., 4, Jan. 1, 2006, pp. 935-937, XP009068822.

Hite B H. “The effect of pressure in the preservation of milk”, West Virginia Agricultural Experiment Station Bulletin 58, Jun. 1, 1899, pp. 1-31, XP055900322.

Jiang Bin et al. “Effects of High Hydrostatic Pressure on Rheological Properties of Rice Starch”, International Journal of Food Properties, vol. 18, No. 6, Dec. 2, 2013, pp. 1334-1344, XP055900332.

* cited by examiner

HIGH PRESSURE-PROCESSED ARCHITECTURAL COATING COMPOSITIONS AND METHODS FOR HIGH PRESSURE-PROCESSING OF ARCHITECTURAL COATING COMPOSITIONS

FIELD OF THE INVENTION

This invention generally relates to architectural coatings, including but not limited to paints and stains, that have been pasteurized or sterilized by high pressure processing to remove or sufficiently reduce the level of bacteria, fungi, yeasts, and/or other biological agents in architectural compositions and to methods for pasteurizing or sterilizing same.

BACKGROUND OF THE INVENTION

Due to environmental and health concerns, there has been a movement toward reducing the amount of volatile organic compounds (VOCs) in paints, stains, and other architectural coating compositions, which evaporate into the environment upon paint film formation. Additives to paints that facilitate or impart desirable paint properties, such as better film coalescence, better resistance to blocking, better film durability, better physical and chemical scrub resistance, and tougher coatings, among others, also contain VOCs. The evaporation of VOCs often results in undesirable aromas, and exposure to such fumes, particularly in areas that are not well ventilated, remains a health concern. Thus, less volatile or non-volatile additives, as well as colorants, that impart comparable (or superior) properties to the paints have been used to replace higher VOC additives. The quest for low VOC paints or a better "green paint" is discussed in a New York Times newspaper article entitled "The Promise of Green Paint" (Kershaw, Sarah, The New York Times, May 15, 2008, p. F6), which is incorporated herein by reference in its entirety.

The reduction of VOC in paints, stains and other architectural coatings and in additives, however, has produced environmentally friendly paints that are more inviting to bacteria, algae, yeasts, fungi and other biological agents that thrive in an aqueous environment. These biological agents grow and die in paint cans and containers, and often impart an unpleasant odor and render paints unusable for its intended purpose, and can cause viscosity loss, discoloration, gassing, frothing, sedimentation and pH changes. Biological agents also present potential health issues. Certain biological agents, such as algae and molds, may grow on dried paint films covering walls or other substrates.

Biocides have been used in aqueous paints or stains to control biological agents inside cans and containers. Some of the biocides may remain on the dried paint film to control algae and molds. However, there is a desire to minimize the level of biocides in aqueous paints/stains or dried paint/stain films while preventing the unimpeded growth of biological agents.

Pasteurization of paints and stains has been attempted. U.S. Pat. No. 5,529,749 to Rinno et al. teaches using dielectric heating, specifically microwaves, to reduce the microbe count in paint compositions. Rinno also teaches that sterilization of paint compositions by direct heating to 80° C.-121° C., even for a short period of time, produces coagulations or additional cross-linking in the paint compositions. Rinno also teaches that sterilization of paint compositions by gamma rays produces hydrogen peroxide and hydroxyl radicals and causes premature cross-linking of the polymer in the paints. Rinno concludes that direct heating and gamma rays are unsuitable for industrial sterilization of paint compositions.

Commonly owned U.S. Pat. No. 10,639,386 to Sheerin et al. contradicts the conclusions of Rinno. Sheerin through experimentation teaches that successful pasteurization or sterilization of paint and stain compositions can take place at significantly lower temperatures, e.g., from about 49° C. to about 72° C. (120° F. to 162° F.), from at least 120 minutes to at least 2 minutes, respectively. Sheerin also through experimentation teaches that gamma rays can successfully pasteurize paint compositions at less than about 15 kGys without further polymerization or cross-linking of the latex polymers in paints.

The following biological agents can be found in paints:

i. Bacteria: *Pseudomonas* species, including *Pseudomonas aeruginosa*; gram negative rod bacteria; *Enterobacter aerogenes; Sphingomonas paucimobilis*; other gram positive and gram negative species etc.

ii. Yeasts: *Candida lambica* and *Yarrowia lipolytica*, etc.

iii. Fungi (molds): *Aspergillus* species, *Acremonium* species, *Geotrichum* species and *Penicillium* species, etc.

In some of the examples or experiments discussed in Sheerin, an inoculum comprising the above listed biological agents was introduced into paints or paint containers and the biological agents are allowed to grow. Thereafter, the paints are pasteurized by heat or gamma rays, and the paints are re-tested to determine the residual concentration of biological agents (if any) and whether the paints remain functional. In other examples or experiments, commercial paints with biocides that were overwhelmed by one or more known biological agents are pasteurized and re-tested to determine whether contaminated paints can be returned to the commercial conditions and be suitable for sale.

*Pseudomonas aeruginosa* or *P. aeruginosa* was found in some contaminated paints. This bacterium is commonly found in wet and warm environments, such as swimming pools and hot tubs. It has been reported by researchers from schools of medicine and public health that *P. aeruginosa* can grow in the range of 25° C. to 42° C. but can be killed at a temperature of 60° C., and up to 70° C. for a duration of about 30 minutes. *P. aeruginosa* does not grow, but does not die, at temperature of 10° C. up to 15° C. or 20° C. These results were reported by A. Tsuji, Y. Kaneko, K. Takahashi, M. Ogawa and S. Goto, "*The Effects of Temperature and pH on the Growth of Eight Enteric and Nine Glucose Non-Fermenting Species of Gram-Negative Rods*," Toho University School of Medicine, Department of Microbiology, Microbiol. Immunol, Vol. 26(1), 15-24, 1982 at pp. 15-24, which is incorporated herein by reference in its entirety.

Tsuji et al. also reported the effects of heat on the following bacteria.

TABLE 1

| | Bacteria Species | Survival T(° C.)‡ | Growth T(° C.)† | Peak T(° C.) |
|---|---|---|---|---|
| 1 | *E. Coli* | 10-50 | 18-47 | 40 |
| 2 | *K. pneumoniae* | 10-50 | 16-48 | 36 |
| 3 | *S. marcescens* | 10-50 | 19-41 | 35 |
| 4 | *P. aeruginosa* | 10-50 | 25-42 | 37 |
| 5 | *P. cepacia* | 10-50 | 28-37 | 34 |
| 6 | *P. fluorescens* | 10-40[1] | 25-32 | 30 |
| 7 | *P. maltophilia* | 10-50 | 22-39 | 34 |
| 8 | *A. xylosoxidans* | 10-40[2] | 28-37 | 35 |
| 9 | *A. calcoaceticus* | 10-50 | 20-45 | 38 |

TABLE 1-continued

| | Bacteria Species | Survival T(° C.)‡ | Growth T(° C.)† | Peak T(° C.) |
|---|---|---|---|---|
| 10 | *A. faecalis* | 10-40[2] | 28-37 | 36 |
| 11 | *F. meningosepticum* | 10-50 | 24-37 | 33 |
| 12 | *Moraxella* | 10-40[3] | 23-35 | 30 |
| 13 | *P. mirabilis* | | 23-44 | 37 |
| 14 | *P. vulgaris* | | 22-41 | 37 |
| 15 | *P. morganii* | | 23-42 | 36 |
| 16 | *P. rettgeri* | | 24-43 | 36 |
| 17 | *P. inconstans* | | 22-45 | 38 |

(*E.* is the genus *Escherichia*; *K.* is the genus *Klebsiella*; S. is the genus *Serratia*; *P.* is the genus *Pseudomonas*; *A.* is the genus *Acinebacter*; *F.* is the genus *Flavobacterium*.)

‡= survive for at least 6 hours; survival tests conducted at 10-70° C. at increments of 10° C.

[1]= survive at 50° C. for about 1 hour.

[2]= survive at 50° C. for about 4 hours.

[3]= survive at 50° C. for about 2 hours.

†= growth tests conducted at 10-50° C. and the time for growth from $10^2$ cells/ml initial concentrations to $10^7$ cells/ml was noted; bacteria growths were observed for 48 hours.

All of the tested bacteria were eradicated at temperature of 60° C. or 70° C. for duration of 30 minutes. No bacteria survived at 60° C. for more than 2 hours. None survived more than 30 minutes at 70° C.

All of the tested bacteria survived at 10° C. but did not grow. Otherwise, they grow at the reported temperature ranges, and the peak or optimal growth temperatures are also reported.

Tsuji et al. also reported that at pH from 6.4 to 8.2 has little effect on the growth rate of these bacteria. However, S. Bricha, K. Ounine S. Oulkheir, N. E. El Haloul and B. Attarassi, "Heat Resistance of *Pseudomonas Aeruginosa* in Preparations at the Base of Cucumber, Tomato and Lettuce as Affected by pH and Sodium Chloride," Ibn Tofail University, Morocco, ISPROMS ISSN: 1994-5108, WJBR Vol. 3, Issue 1, at 1-8, reported that at pH of about 2 a strain of *P. aeruginosa*'s heat resistance is diminished at temperature of 63° C., but the heat resistance of *P. aeruginosa* at pH of 4.5 and 6 is about the same. Bricha et al. also reported that at low pH sodium chloride salt at 2-6% may protect the bacteria. Bricha et al. is incorporated herein by reference in its entirety.

Yeast cells begin to die at temperature greater than 50° C. and most would die at temperatures from about 55° C. to about 60° C. It is well known to bakers that yeasts when added to water that is too warm are killed and the dough won't rise. At temperatures of 10° C. or lower, yeasts would not grow. Yeasts grow in the temperature range from about 27° C. to about 32° C. depending on the species. Hence, yeasts have a similar dormant-growth-death temperature profile as the bacteria discussed above. Hence, yeasts can be eradicated and/or controlled by the heat method including storage and transportation, described in Sheerin.

Molds including mildew, fungi, and common molds exist in the same temperature range (and relative humidity) that supports human life. Hence, mold and mold spores are ubiquitous in our environment. Molds can grow in temperatures between 4° C. and 38° C. (40°-100° F.). Below 4° C., molds are in a dormant state and are revived when the temperature warms up with the proper relative humidity. Some molds survive temperature as high as 38° C. or higher. The dormant-growth-death temperature regime for several molds and spores has been reported, as shown below. See http://www.thermapure.com/environmental-services/mold/.

TABLE 2

| Mold species | Lethal T(° C.) | Duration (min) |
|---|---|---|
| *Alternarie altermata* | 63 | 25 |
| *Aspergillus fumigatus* | 65 | 30 |
| *Aspergillus niger* | 63 | 25 |
| *Chaetomium globosum* | 57 | 10 |
| *Cladosporium herbarum* | 50 | 10 |
| *Stachybotrys chartarum* | 60 | 30 |

While some lethal temperatures are slightly higher than 60° C. for some of the mold discussed above, the time duration to kill is significantly shorter. At 60° C. but for longer time duration, most molds can be killed. Hence, molds can be eradicated and/or controlled by the same heating method described in Sheerin.

As taught by Rinno and Sheerin, which are incorporated herein by reference in their entireties, pasteurization or sterilization of paint and stain compositions by various methods are unpredictable. Detailed analysis and experimentation are necessary to determine the efficacy of any pasteurization technique. High pressure processing (HPP), also known as pascalization, bridgmanization, or cold pasteurization, has been used to pasteurize certain foods and drinks. However, its use in pasteurization of paint and stain compositions has not been recognized, and it is unknown heretofore whether HPP causes negative effects on architectural compositions, such as coagulation or additional cross-linking by the latex polymers.

Hence, there remains a need for additional sterilization or pasteurization techniques of architectural compositions such as paints and stains.

SUMMARY OF THE INVENTION

Hence, the invention relates to a method for pasteurizing paints with high pressure with or without an energy source, such as heat to kill any agents that may have been introduced into the paints.

An embodiment of the present invention relates to a method for reducing biological agents in an architectural coating composition comprising the steps of (i) preparing the architectural coating composition; and (ii) applying a pressure source from about 50 MPa to about 1,000 MPa, preferably from about 300 MPa to about 700 MPa, or from about 400 MPa to about 700 MPa or from 450 MPa to about 650 Mpa, to said architectural composition for a duration of up to about 10 minutes, preferably about 1 to about 5 minutes or from about 3 to about 5 minutes or from about 2 minutes to about 4 minute or from about 2.5 minutes to about 3.5 minutes, to sufficiently reduce the biological agents.

Preferably, the architectural composition is stored in flexible containers before step (ii). Void space, if any, in the containers should be less than about 10% of the volume of the flexible container, preferably less than about 5% or less than about 2.5%.

Preferably, the flexible container is made from a material selected from polyethylene terephthalate (PET), amorphous PET (APET), crystalline PET (CPET), high density polyethylene (HDPE), low density polyethylene (LDPE) or polypropylene (PP).

The flexible container may have a film seal, which preferably is made from PP, PE, HDPE, PP, or other material.

Optionally, the method for reducing biological agents further comprises a heating step either simultaneously or sequentially with step (ii).

Optionally, the method for reducing biological agents further comprises a second pressure treating step. The second pressure treating step may be at the same pressure and duration as those in step (ii). Alternatively, the second pressure treating step may be at different pressure and/or duration as those in step (ii).

Optionally, the method may also include a step of adding a biocide or antimicrobial component to the architectural composition, preferably at a lower amount than untreated or unpasteurized an architectural composition.

Preferably, the eradication is at least a 3-log (99.9%) reduction, preferably a 4-log (99.99%) reduction and more preferably a 5-log (99.999%) or more reduction

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

Figure 1A:
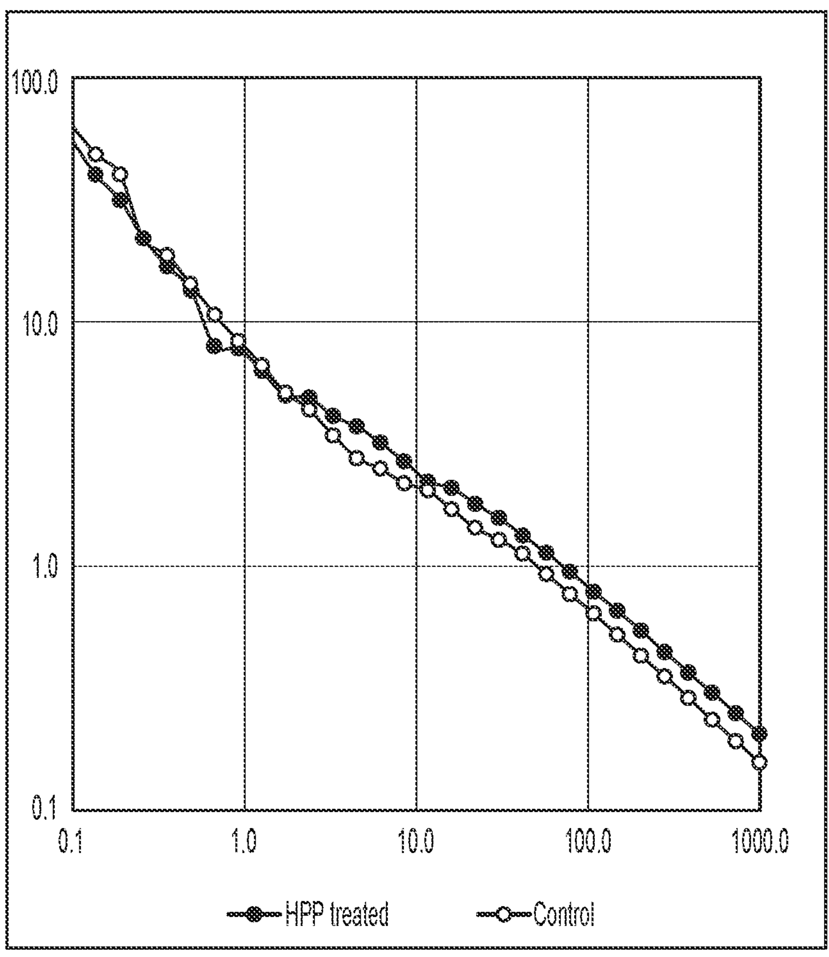
FIGS. 1(*a*)-1(*c*) are the flow curves of three commercial paints with and without HPP treatment on a log-log scale of the viscosity of the paint samples (Y-axis, Pascal seconds, or Pa-s) as a function of the applied shear rate or shear stress (X-axis, second$^{-1}$).

As used herein, paint or paints include aqueous or water-based paint compositions, stains or other architectural compositions. Architectural compositions also include materials understood in the art as architectural compositions, such as adhesives, caulking, asphalts, etc. The pasteurization or sterilization techniques utilizing HPP described herein are applicable to all architectural compositions. Paint film(s) means paint(s) or stain(s) that have been applied on a surface or substrate, and are dried or the latex particles in the paint(s) have cross-linked to form a film.

As discussed above, water-based latex architectural coatings, such as paints, stains, other household, and industrial coatings, have become more environmentally friendly. This means that modern day architectural coatings have less VOCs in them and have additives and colorants that also have low VOCs. The reduction in VOCs have rendered the architectural coatings more inviting to biological agents, such as bacteria and fungi in the water phase and algae and certain fungi, e.g., molds, in the dried film phase. One solution is to add biocides to the architectural coatings at the latex formation stage, at the pigment dispersion stage, where pigments are dispersed with surfactants, dispersants and water, and/or the let-down stage, where the aqueous latex, the pigment dispersion and additives are combined. The paints are then placed in cans and containers for storage and shipping. Colorants, which may contain their own biocides, are added later at the retail stores to achieve the paint colors that the consumers purchased.

While biocides are useful to preserve paints and other architectural coatings and are useful in the dried paint film to help prevent the growth of biological agents, some environmentally conscientious consumers have expressed a desire for biocide-free or biocide-reduced paints. However, without biocide or with reduced biocides, biological agents could thrive in paints or paint films.

High pressure processing (HPP), also called "cold pasteurization", has been employed to pasteurize certain foods, as reported in K. Considine, A. Kelly, G. Fitzgerald, C. Hill and R. Sleator, "High-pressure Processing—Effects on Microbial Food Safety and Food Quality," FEMS Microbiol. Lett. 281 (2008), 1-9, which is incorporated herein by reference in its entirety. In the food industry, HPP is typically conducted between 50 MPa and 1,000 MPa (about 7,250 psi to about 145,000 psi, or 500 bars to 10,000 bars) or more commonly from 300 MPa to 700 MPa for a time duration of a few seconds to several minutes (e.g., about 10 minutes or less) or more commonly from about 1 minute to about 5 minutes, preferably 3 minutes to 5 minutes. HPP generally results in a modest rise in temperature (5-15° C.) through adiabatic heating, and the temperature would return to its original temperature after decompression.

Different microbial organisms react with different degrees of resistance to HPP, and there can be significant differences in HPP sensitivity among bacteria species. Viability losses can vary between 0.5 log and 8.5 logs among pathogenic bacterial strains. In general, prokaryotic cells, which include bacteria, tend to be more pressure resistant than eukaryotes. Morphology also plays a role, which is reflected in the fact that cocci are more resistant than rod-shaped bacteria. In addition, some bacteria such as *Clostridium* and *Bacillus* spp. tend to form endospores when stressed. Endospores tend to be highly resistant to HPP and can withstand treatment of more than 1,000 MPa. Spores of the *Clostridium* spp. are generally more pressure resistant than those of the *Bacillus* spp.

HPP at a lower pressure can induce germination of bacterial spores; interestingly, these spores were found to be more sensitive to subsequent pressure treatment(s). Combination of HPP and heat simultaneously or sequentially, or pressure cycling treatments have achieved spore inactivation to some degrees. Gram-positive bacteria are more resistant to heat and pressure than gram-negative bacteria. The efficacy of microbial reduction depends on factors, such as bacterial species, number of treatment cycles, pH, pressure, processing time and temperature.

Yeasts and molds are relatively HPP sensitive, except that ascospores of heat-resistant molds (e.g., *Byssochlamys, Neosartorya*, and *Talaromyces*) are highly HPP resistant. Pressure resistance of viruses varies considerably.

$Ca^{2+}$ ions and other cations protect *E. coli* from the effects of HPP, as well as high sucrose; NaCl and $CaCl_2$ protect *Bacillus coagulans* more than nonionic solutes, such as sucrose and glycerol. Low pH in a suspending medium may render certain pathogens more sensitive to HPP. On the other hand, HPP may not be as effective for low acid materials, because low acidity retains spores unless heat is added. pH of acidic solution may reversibly decrease as pressure increases but reverts back during decompression. Since HPP may not kill spores, bacteria can return.

Treatments at temperatures below ambient, e.g., at refrigeration level, can enhance HPP and can achieve lower microbial numbers than HPP at 25° C. (77° F.) or room temperature. Similarly, using HPP in combination with mild heat treatments can give better results than either method used individually. In one reported example, a pressure-resistant *E. coli* was inactivated in a HPP treatment of 400 MPa and 50° C. for 15 minutes. Neither treatment alone could achieve the reported inactivation (5-6 log reduction). Bacterial spores can be inactivated by first treating with low HPP followed by relatively mild heat treatments (see e.g., J. Food Prot. 2013, 76(3), pp. 448-55).

Without being restricted to any particular theory, pressure treatment induces changes in the bacterial cells, including inhibition of enzymes and protein synthesis, and alterations in cell morphology and cell membrane. Pressure treatment also disrupts processes such as transcription, translation, and cellular functions responsible for survival and reproduction. Bacterial membrane damage may cause leakage of cellular material through the inner and outer membrane and nutrient uptake and disposal of cell waste.

HPP can be combined with other antimicrobial agents, including but not limited to lacitin 3147, lactoperoxidase, and nisin, typically used in foods. HPP can also be used with antimicrobial agents typically used in paints and stains.

One aspect of the present invention is to pasteurize or sterilize paints, stains and other architectural coatings, such as adhesive, caulks, and the like, so that the growth of biological agents is either obviated or limited in the absence of biocide or with reduced biocide. In a preferred embodiment, the architectural compositions, such as paints and stains, are pasteurized with high pressure with or without an energy source, preferably heat or radiation sources (including but not limited to gamma ray, infrared, ultraviolet, electron beam and microwave radiation), during or after the manufacturing process to significantly reduce the population of biological agents, if any, that exist in the architectural compositions. Preferably, paint, stain and the other architectural compositions are stored in flexible containers that preferably can transfer the high pressure to the compositions contained therein. These containers may be the quart, pint, gallon, or 5-gallon liners or flexible containers that can be sold to consumers or that are optionally stored in substantially rigid containers that are sold to consumers. In a preferred embodiment, the containers are large liners, e.g., 20-gallon or 50-gallon capacity, made from flexible materials and the HPP treated architectural coatings are transferred to the smaller containers to be sold to consumers. These paint containers are then stored until sold to the customers. In most situations, the paint containers are shipped to and stored at paint distribution centers, and then shipped and stored at retail stores before being purchased by consumers. An advantage of storing the pasteurized architectural compositions in flexible containers is that it is easier for the consumers to mix the paints or stains before use by turning, rotating or squeezing the flexible containers.

HPP-proof containers used in the food industry could function as HPP-proof paint/stain containers. It is preferred that that these containers be resized to hold paint/stain volumes normally sold to consumers, e.g., pints, quarts, gallons, etc. The HPP-containers should have a reliable seal to prevent pressurized water/liquid from entering the containers and should be made from a flexible, durable material to withstand extreme pressures encountered during HPP treatment. Preferably, the air pocket within any HPP-container is minimized, preferably to less than about 10% of total volume and preferably less than about 5% or less than about 2.5%. Typical HPP-proof containers can be bottles with film seals/caps, pouches, cups/tubs/trays with a top film seal, or vacuum bags. Suitable flexible, durable materials include, but are not limited to polyethylene terephthalate (PET), amorphous PET (APET), crystalline PET (CPET), high density polyethylene (HDPE), low density polyethylene (LDPE), polypropylene (PP). Suitable film seals materials include but are not limited to PP, PE, HDPE, PET, etc.

It is known through pasteurization of foods that HPP does not disrupt covalent bonds, but only affects non-covalent, or physical bonds, such as ionic and hydrogen bonds and hydrophobic interactions. The latex particles or latex resin that form paint films are formed mostly through covalent bonds are therefore not expected to be degraded by HPP. However, the high pressure could in theory result in a loss in colloidal stability, and subsequent irreversible coagulation. In addition, some of the rheological modifiers, such as thickeners and surfactants interact with the latex resin through hydrophobic interactions and hydrogen bonds. Hence, HPP may affect the viscosities of the architectural compositions, which can degrade the performance of paints and stains and other architectural compositions.

Figure 1B:
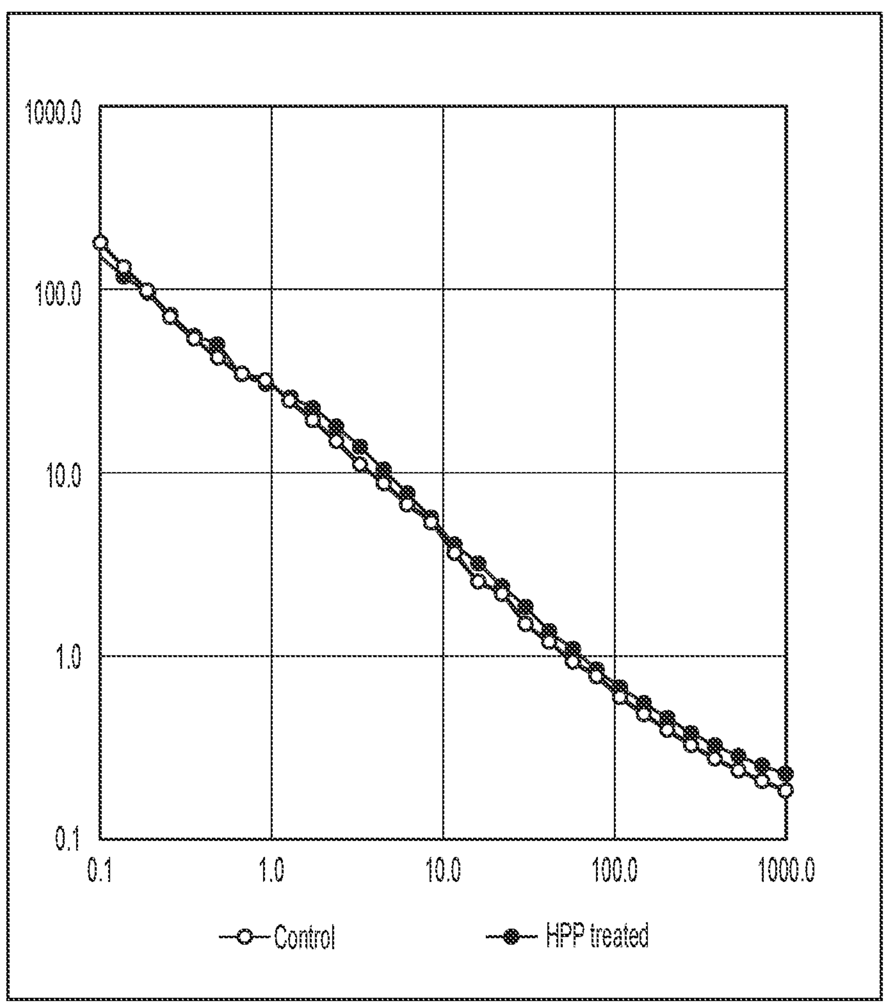
Figure 1C:
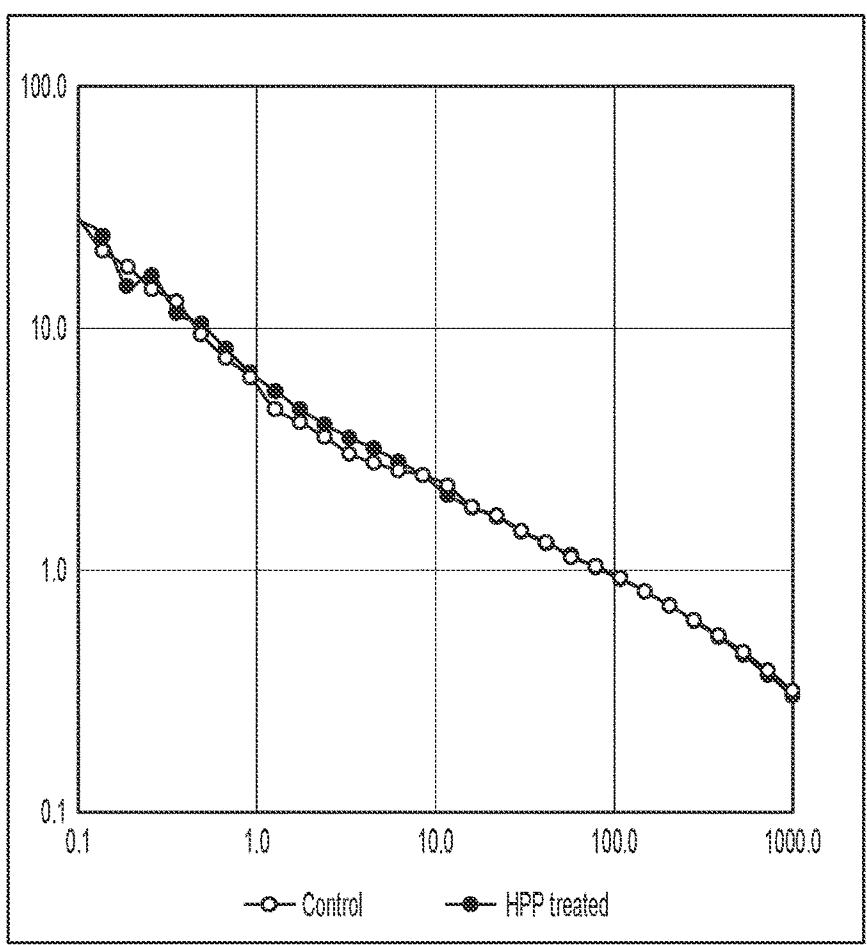

12-ounce HPP-proof juice bottles were filled with three commercial paints, Commercial 1 (a deep base primer), Commercial 2 (a 1-base paint with flat finish), and Commercial 3 (a 4-base paint with semi-gloss finish), and subjected to HPP treatment at 86,587 psi (597 MPa), for a duration of 3 minutes at 52° F., described further below. The standard HPP treatment for foods is 85,000 psi (586 MPa) for 3 minutes. The rheological properties of these HPP-treated commercial paint samples were compared to the untreated samples or controls, and the results are shown in FIGS. 1(*a*)-(*c*). Flow curves are plotted on log-log scales of the viscosity of the paint samples (Y-axis, Pascal seconds) as a function of the applied shear rate or shear stress (X-axis, second$^{-1}$). Viscosity quantifies the compositions' resistance to flow. The shear rate is the change in strain over the change in time. The viscosities of the samples (vertical axis) were measured at different sheer rate (spin speed) (horizontal axis). Low spin speed mimics the stage when the paint is at substantially static conditions. At this stage, high viscosity is desirable indicating low color flow and low color separation. High spin speed mimics the stage when a user is applying the paint onto a surface, e.g., moving paint brushes or rollers. At this stage, low viscosity is desirable indicating easier application. FIGS. 1(*a*)-(*c*) show that the flow curves for all three paint samples are substantially the same between the HPP treated samples and the untreated control samples. The results show that paints and stains can be treated with HPP without loss of physical properties, e.g., rheological properties, and performance.

The static viscosity (in-the-paint-can viscosity) of these commercial paint samples and the HPP treated samples were also measured, as shown in Table 3 below.

TABLE 3

| | Stormer (KU) | | ICI (P) | | pH | |
|---|---|---|---|---|---|---|
| Paint | Spec | Actual | Spec | Actual | Spec | actual |
| Commercial 1 control | 95.0- | 95.3 | N/A | 0.787 | 8.30- | 8.6 |
| Commercial 1- HPP | 98.0 | 93.0 | | 0.767 | 8.80 | 8.5 |
| Commercial 1- HPP | | 93.4 | | 0.792 | | 8.5 |
| Commercial 2 control | 92.0- | 98.0 | 1.000- | 1.125 | 8.60- | 8.3 |
| Commercial 2 - HPP | 96.0 | 99.0 | 1.300 | 1.179 | 8.80 | 8.6 |
| Commercial 2 -HPP | | 99.6 | | 1.246 | | 8.6 |
| Commercial 3 control | 100.0- | 103.4 | 1.100- | 0.913 | 8.60- | 8.9 |
| Commercial 3 - HPP | 106.0 | 103.0 | 1.350 | 0.908 | 9.20 | 8.8 |
| Commercial 3 - HPP | | 104.6 | | 0.950 | | 8.8 |

As shown, the Stormer and ICI viscosities of the HPP treated samples are very close to the untreated samples, showing that the HPP treatment does not significantly affect the viscosity of the paints, from which can be inferred that HPP treatment does not significantly affect the physical bonds of the thickeners, surfactants or other rheological modifiers used in commercial paints.

In another experiment, about 2 gallons of a paint (a 4-base paint with semi-gloss finish) were inoculated with a combination of microbial species (see Table 4). The inoculated paint was deposited in 12-ounce HPP proof juice bottles.

The majority of the samples was treated with HPP at 86,587 psi for 3 minutes at 52° F., while some samples were not treated and kept as controls. Two of these samples, one being an HPP treated sample, and the other one a non-treated control, were tested for biological activities. Both of these samples had a headspace of about 0.5-inch. It is believed that the amount of headspace is a factor in HPP treatment, because it would take more time to compress the air in the headspace and could therefore result in an increase in processing time.

TABLE 4

| Organism | Type | Attribute | Morphology | Spore-former (Y/N) |
|---|---|---|---|---|
| *Pseudomonas aeruginosa* | Gram-negative bacteria | aerobic | Rod | N |
| Gram-negative rod (grey) | Gram-negative bacteria | aerobic | Rod | N |
| *Pseudomonas pseudoalcaligenes* (in *P. aeruginosa* group) | Gram-negative bacteria | aerobic | Rod | N |
| Proteus vulgaris (nitrate-reducing, HS-producing) | Gram-negative bacteria | aerobic & facultative anaerobic | Rod | N |
| *Brevundimonas diminuta* | Gram-negative bacteria | aerobic | Rod | N |
| *Pseudomonas mendocina* | Gram-negative bacteria | aerobic | Rod | N |
| *Shewanella putrefaciens* | Gram-negative bacteria | facultative anaerobic | Rod | N |
| *Pseudomonas fluorescens* | Gram-negative bacteria | aerobic | Rod | N |
| *Aspergillus* species | Mold | highly aerobic | N/A | Y |
| *Penicillium* species | Fungus | strictly aerobic | N/A | Y |
| *Escherichia coli* | Gram-negative bacteria | facultative anaerobic | Rod | N |
| *Pseudomonas putida* | Gram-negative bacteria | aerobic | Rod | N |
| *Burkholderia cepacia* | Gram-negative bacteria | aerobic | Rod | N |
| *Staphylococcus aureus* | Gram-positive bacteria | facultative anaerobic | Cocci | N |
| *Alcaligenes faecalis* (aka *Bordetella avium*) | Gram-negative bacteria | aerobic | Rod | N |
| *Aspergillus oryzae* | Mold | aerobic | N/A | Y |
| *Cladosporium cladosporioides* | Mold | aerobic | N/A | Y |
| *Geotrichum candidum* | Fungus | aerobic | N/A | Y |
| *Paecilomyces variotti* | Mold | aerobic | N/A | Y |
| *Penicillium ludwigii* | Fungus | strictly aerobic | N/A | Y |
| *Sporothrix* species | Fungus | aerobic | N/A | Y |
| *Trichoderma viride* | Fungus | aerobic | N/A | Y |

The biological activity results for the HPP treated paint sample versus the control, non-treated paint sample are shown in Tables 5(a)-(b). Aerobic plate count (APC) is an indicator of bacterial population on a sample and is measured in "cfu/g" unit, which stands for colony forming units per gram of sample. APC assumes that each cell would form a visible colony when mixed with agar containing the appropriate nutrients. It is a generic test for organisms that grow aerobically or requiring oxygen at mesophilic or moderate temperature (25-40° C. or 77-104° F.).

The APC results in the Tables below were obtained with a 1:10 dilution, by mixing 1 gram of product with 9 ml of phosphate buffered saline (PBS) as a diluent. Of the resulting mixture, 1.0 ml was plated onto two plates. Trypticase soy agar (TSA) was poured in one plate, and sab dextrose (SAB) in the other. The TSA will grow bacteria, and the SAB will grow yeast and mold, although some gram negative bacteria will also grow in the SAB agar.

The colonies that grew on the plates were counted, keeping in mind that a 1:10 factor needed to be applied, since samples were diluted. For example, 5 colonies counted equals 50 colonies present per gram of original product sample.

The control sample (no HIPP treatment) was plated with several dilutions, since the initial growth was too dense to be counted; the dilutions therefore permitted an accurate count for the original sample.

TABLE 5a

| | Aerobic Plate Count (APC) | | | | | |
|---|---|---|---|---|---|---|
| | cfu/g | Gram+ (cfu/g) | Type | Gram− (cfu/g) | Type | Sab Dextrose (cfu/g) |
| Inoculated Control (no HPP) | 1,270,000 | No | N/A | 1,270,000 | Rod | 1160 (G-Rod) 20 (mod) |
| | *** ENRICHMENT *** | | | | | |
| | *E-coli* | *S. aureus* | *P. aeruginosa* | *Salmonella* | | Sab Dextrose |
| | negative | negative | presumptive | negative | | G-Rod |
| | Trypto Soy Agar: | | Gram+ | Type | Gram− | Type |
| | | | No | N/A | Yes | Rod |

TABLE 5b

| | Aerobic Plate Count (APC) | | | | | |
|---|---|---|---|---|---|---|
| | cfu/g | Gram+ (cfu/g) | Type | Gram− (cfu/g) | Type | Sab Dextrose (cfu/g) |
| Inoculated and HPP treated | 30 | Yes | rod | | | <10 |
| | *** ENRICHMENT *** | | | | | |
| | *E-coli* | *S. aureus* | *P. aeruginosa* | *Salmonella* | | Sab Dextrose |
| | negative | negative | negative | negative | | No growth |
| | Trypto Soy Agar: | | Gram+ | Type | Gram− | Type |
| | | | Yes | Rod | | |

The APC does not tell exactly what types of bacteria are present; it is a quantitative test. That is why an enrichment test was used, which is a qualitative test; 10 grams of product was added to a jar containing 90 mL of letheen broth, and the mixture was incubated for 48 hours. Next, differential media were used, wherein each is an indicator to specific bacteria by changing the color of the media, or the color of the growth on the media. Media that were used are specific for *E. coli, S. aureus, P. aeruginosa*, and *Salmonella*. A drop of broth was introduced to each medium with a loop.

The analysis showed that the APC was reduced from 1,270,000 cfu/g before HPP treatment to about 30 cfu/g residual, which represents nearly a 5-log reduction (99.998%) in bacterial colonies. Preferably, the eradication is at least a 3-log (99.9%) reduction, preferably a 4-log (99.99%) reduction and more preferably a 5-log (99.999%) or more reduction. The residual bacterial count in the HPP-treated sample was identified as gram positive (gram+) bacteria. It is likely that the Gram+ bacteria are a contamination introduced through handling of the sample, since the enrichment test was negative for *S. aureus*, which is the only Gram+ species present in the mixture of microbial species that was used as the inoculum. Furthermore, no gram+ bacteria were detected in the control/no HPP treatment sample.

Hence, the experiments above show that (i) paint and stain compositions, as well as the other architectural compositions, can be treated by HPP and maintain their functionalities, and (ii) HPP treatment can reduce the bacterial count in paint and stain compositions up to a 5-log reduction.

Figure 2:
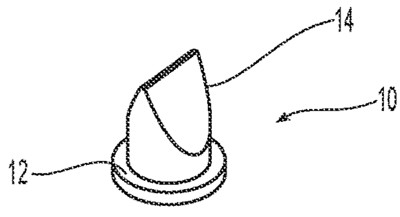
FIG. 2 shows a perspective view of an exemplary one-way flow valve.

In accordance with another embodiment of the present invention, the HPP suitable paint containers are capable of having colorants added to treated paints within the containers. Commonly owned U.S. Pat. No. 9,994,722 discusses that a gallon (128 ounces) paint can could have up to 24 ounces of free space reserve for colorants. This represents an air space of about 18.75%. As discussed above, for this amount of free space HPP treatments would take longer and be more expensive. In this embodiment, a flexible or elastomeric pouch or bag is partially filled and due to its flexibility or stretchability, the pouch or bag can hold the paint at less than full capacity without having a significant air space within the pouch or bag to maximize the HPP treatments. The inventive pouch or bag would have a one-way valve, such as a duckbill valve (10) shown in FIG. 2. Valve 10 has a base 12 and tapered end 14, which would be located inside the HPP pouch or bag. Any hollow tube can be pushed into base 12 to open tapered end 14 to add colorants to the treated paints up to the pouch or bag's volumetric capacity. During the HPP treatments, the internal pressure of the pouch or bag would be evenly distributed therein and this pressure would act on tapered end 14 to fully close valve 10. Higher pressure would cause higher force to keep valve 10 closed. It is expected that duckbill valve 10 would keep the pouch or bag sealed during the HPP treatment and would allow colorants to be added to the treated paints. Duckbill valves are commonly used on athletic balls, such as footballs, basketball, soccer balls, etc., as well as flood drainage pipes and sewage systems.

Paints and stains and other architectural compositions can be pasteurized by HPP in a batch process with the paints and stains stored inside flexible containers being pressurized in batches, as described above, or in a more continuous fashion, e.g., in-line HPP, followed by aseptic filling in soft or rigid, flexible or metal containers that are sold to consumers.

Preferably, the storage of paint in step (iii) includes storing the paint containers in an environment in which bacteria, if present, do not grow. As discussed above, at 10° C. a large number of bacteria do not grow. Additionally, the temperature growth range of these bacteria is above 15° C., and very few bacteria would grow at a temperature of 20° C. Hence, preferably the paints are stored at temperature of 20° C. (68° F.) or lower, more preferably at temperature of 15° C. (59° F.) or lower, or more preferably at temperature of 10° C. (50° F.) or lower. These preferred storage temperatures can be achieved with conventional air conditioning technology. Additionally, it is preferred that during transportation the paints are also kept at these temperature ranges.

While it is apparent that the illustrative embodiments of the invention disclosed herein fulfill the objectives stated above, it is appreciated that numerous modifications and other embodiments may be devised by those skilled in the art. Therefore, it will be understood that the appended claims are intended to cover all such modifications and embodiments, which would come within the spirit and scope of the present invention.

What is claimed is:

1. A method for reducing biological agents in an architectural coating composition, including at least one of paint and stain compositions, comprising the steps of (i) preparing the architectural coating composition;

(ii) applying a pressure ranging from 50 MPa to 1,000 MPa, to said architectural coating composition for a duration of up to 10 minutes; and (iii) then storing the architectural coating composition in paint containers that are sold to consumers.

2. The method of claim 1 further comprising (vi) applying a radiation step, including gamma ray, infrared, ultraviolet, electron beam or microwave radiation.

3. The method of claim 1 further comprising (vii) adding a biocide or antimicrobial agent to the architectural coating composition.

4. The method of claim 1, wherein the reduction of the biological agents is at least a 3-log (99.9%) reduction.

5. A method for reducing biological agents in an architectural coating composition, including at least one of paint and stain compositions, comprising the steps of (i) preparing the architectural coating composition; and (ii) applying a pressure ranging from 300 MPa to 700 MPa, to said architectural coating composition for a duration of up to 10 minutes.

6. The method of claim 5, wherein the pressure ranges from 400 MPa to 700 MPa.

7. The method of claim 5, wherein the pressure ranges from 450 MPa to 650 MPa.

8. A method for reducing biological agents in an architectural coating composition, including at least one of paint and stain compositions, comprising the steps of (i) preparing the architectural coating composition; and (ii) applying a pressure ranging from 50 MPa to 1,000 MPa, to said architectural coating composition for a duration ranging from 1 minute to 5 minutes.

9. The method of claim 8, wherein the duration ranges from 3 minutes to 5 minutes.

10. The method of claim 8, wherein the duration ranges from 2 minutes to 4 minutes.

11. The method of claim 8, wherein the duration ranges from 2.5 minutes to 3.5 minutes.

12. A method for reducing biological agents in an architectural coating composition, including at least one of paint and stain compositions, comprising the steps of (i) preparing the architectural coating composition; and (ii) applying a pressure ranging from 50 MPa to 1,000 MPa, to said architectural coating composition for a duration of up to 10 minutes;

wherein the architectural coating composition is stored in a flexible container before step (ii) and the flexible container transfers the pressure to the architectural coating composition contained therein.

13. The method of claim 12, wherein a void space within said flexible container is less than 10% of the volume of the flexible container.

14. The method of claim 13, wherein the flexible container is made from a material selected from polyethylene terephthalate (PET), amorphous PET (APET), crystalline PET (CPET), high density polyethylene (HDPE), low density polyethylene (LDPE) or polypropylene (PP).

15. The method of claim 12, wherein said flexible container comprises a film seal.

16. The method of claim 15, wherein the film seal is made from a material selected from polypropylene, polyethylene, high density polyethylene or polyethylene terephthalate.

17. A method for reducing biological agents in an architectural coating composition, including at least one of paint and stain compositions, comprising the steps of (i) preparing the architectural coating composition;

(ii) applying a pressure ranging from 50 MPa to 1,000 MPa, to said architectural coating composition for a duration of up to 10 minutes; and (iii) applying a heating step, either simultaneously or sequentially with step (ii).

18. The method of claim 1 or 17 further comprising (v) applying a second pressure treating step.

19. The method of claim 17 further comprising (iv) applying a second pressure treating step at the same pressure and duration as those from step (ii).

20. A method for reducing biological agents in an architectural coating composition, including at least one of paint and stain compositions, comprising the steps of (i) preparing the architectural coating composition;

(ii) applying a pressure ranging from 50 MPa to 1,000 MPa, to said architectural coating composition for a duration of up to 10 minutes; and (iii) applying a second pressure treating step at the same pressure and duration as those from step (ii).

* * * * *